(12) United States Patent
Saffarian et al.

(10) Patent No.: US 12,084,674 B2
(45) Date of Patent: Sep. 10, 2024

(54) METHODS AND COMPOSITIONS FOR A HIV BASED DELIVERY SYSTEM

(71) Applicant: University of Utah Research Foundation, Salt Lake City, UT (US)

(72) Inventors: Saveez Saffarian, Salt Lake City, UT (US); Mourad Bendjennat, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 360 days.

(21) Appl. No.: 17/065,101

(22) Filed: Oct. 7, 2020

(65) Prior Publication Data

US 2021/0102221 A1 Apr. 8, 2021

Related U.S. Application Data

(60) Provisional application No. 62/911,812, filed on Oct. 7, 2019.

(51) Int. Cl.
*C12N 15/86* (2006.01)
*C12N 15/113* (2010.01)
*C12Q 1/70* (2006.01)

(52) U.S. Cl.
CPC ............ *C12N 15/86* (2013.01); *C12N 15/113* (2013.01); *C12Q 1/703* (2013.01); *C12N 2310/14* (2013.01); *C12N 2740/16022* (2013.01); *C12N 2740/16111* (2013.01); *C12N 2740/16222* (2013.01)

(58) Field of Classification Search
CPC .. C12N 15/86; C12N 15/113; C12N 2310/14; C12N 2740/16022; C12N 2740/16111; C12N 2740/16222; C12Q 1/703
See application file for complete search history.

(56) References Cited

U.S. PATENT DOCUMENTS

2017/0362607 A1* 12/2017 Tran ..................... C07K 14/005
2019/0055568 A1* 2/2019 Pule

OTHER PUBLICATIONS

Sweeney, N. P., and Vink, C. A., "The impact of lentiviral vector genome size and producer cell genomic to gag-pol mRNA ratios on packaging efficiency and titre," Molecular Therapy: Methods & Clinical Development 21: 574-584. doi: 10.1016/j.omtm.2021.04.007. eCollection Apr. 16, 2021. (Year: 2021).*
Corey, L. V., et al., "Mutational analysis of the C-terminal gag cleavage sites in human immunodeficiency virus type 1," Journal of Virology 81(18): 10047-10054. doi: 10.1128/JVI.02496-06. Epub Jul. 18, 2007. (Year: 2007).*
GenBank AF324493.2, HIV-1 vector pNL4-3, complete sequence, submitted Nov. 28, 2000 (Year: 2000).*
Ramezani, A., and Hawley, R. G., "Strategies to insulate lentiviral vector-expressed transgenes," Methods in Molecular Biology 614: 77-100. doi: 10.1007/978-1-60761-533-0_5. (Year: 2010).*
Jetzt, A. E., et al., "High rate of recombination throughout the human immunodeficiency virus type 1 genome," Journal of Virology 74(3): 1234-1240. doi: 10.1128/jvi.74.3.1234-1240.2000. Feb. 2000 (Year: 2000).*
Hübner, W., et al., "Sequence of human immunodeficiency virus type 1 (HIV-1) Gag localization and oligomerization monitored with live confocal imaging of a replication-competent, fluorescently tagged HIV-1," J Virol 81(22): 12596-12607. doi: 10.1128/JVI.01088-07. (Year: 2007).*
Baumgärtel V, Ivanchenko S, Dupont A, Sergeev M, Wiseman PW, Kräusslich HG, Bräuchle C, Müller B, Lamb DC (2011) Live-cell visualization of dynamics of HIV budding site interactions with an ESCRT component. *Nat. Cell Biol.* 13, 469-474.
Bendjennat M., Saffarian S (2016) The race against protease activation defines the role of ESCRTs in HIV budding. *PLOS Pathog.* 12, e1005657.
Bleck M, Itano MS, Johnson DS, Thomas VK, North AJ, Bieniasz PD, Simon SM (2014) Temporal and spatial organization of ESCRT protein recruitment during HIV-1 budding. *Proc. Natl. Acad. Sci. USA* 111, 12211-12216.
Briggs JA, Riches JD, Glass B, Bartonova V, Zanetti G, Kräusslich HG (2009) Structure and assembly of immature HIV. *Proc. Natl. Acad. Sci. USA* 106, 11090-11095.
Briggs JA, Kräusslich HG (2011) The molecular architecture of Hiv. *J. Mol. Biol.* 410, 491-500.
Carlson LA, de Marco A, Oberwinkler H, Habermann A, Briggs JA, Kräusslich HG, Grünewald K (2010) Cryo electron tomography of native HIV-1 budding sites. *PLOS Pathog.* 6, e1001173.
Caspar DL, Klug A (1962) Physical principles in the construction of regular viruses. *Cold Spring Harb. Symp. Quant. Biol.* 27, 1-24.

(Continued)

*Primary Examiner* — Robert M Kelly
*Assistant Examiner* — Eric J Rogers
(74) *Attorney, Agent, or Firm* — BALLARD SPAHR LLP

(57) ABSTRACT

Disclosed are nucleic acid sequences comprising a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region. Disclosed are methods of producing a recombinant lentivirus comprising transfecting a cell with a plasmid comprising the nucleic acid sequence of one or more of the disclosed nucleic acid sequences in combination with an envelope plasmid. Disclosed are methods of monitoring lentivirus assembly, budding, and/or maturation comprising transfecting a cell with a plasmid comprising any one of the disclosed nucleic acid sequences in combination with an envelope plasmid, wherein the exogenous sequence of interest encodes a detection agent. Disclosed are methods of treating a subject with a therapeutic agent comprising administering to a subject in need thereof a recombinant lentivirus, wherein the recombinant lentivirus comprises one or more of the disclosed nucleic acid sequences, wherein the exogenous sequence of interest encodes a therapeutic agent.

21 Claims, 4 Drawing Sheets
Specification includes a Sequence Listing.

(56) References Cited

OTHER PUBLICATIONS

Hendrix J, Baumgärtel V, Schrimpf W, Ivanchenko S, Digman MA, Gratton E, Kräusslich HG, Müller B, Lamb DC (2015) Live-cell observation of cytosolic HIV-1 assembly onset reveals RNA-interacting Gag oligomers. *J. Cell Biol.* 210, 629-646.

Hübner W, Chen P, Del Portillo A, Liu Y, Gordon RE, Chen BK (2007) Sequence of human immunodeficiency virus type 1 (HIV-1) Gag localization and oligomerization monitored with live confocal imaging of a replication-competent fluorescently tagged HIV-1. *J. Virol.* 81, 12596-12607.

Ivanchenko S, Godinez WJ, Lampe M, Kräusslich HG, Eils R, Rohr K, Bräuchle C, Müller B, Lamb DC (2009) Dynamics of HIV-1 assembly and release. *PLOS Pathog.* 5, e1000652.

Jouvenet N, Bieniasz PD, Simon SM (2008) Imaging the biogenesis of individual HIV-1 virions in live cells. *Nature* 454, 236-240.

Jouvenet N, Simon SM, Bieniasz PD (2009) Imaging the interaction of HIV-1 genomes and Gag during assembly of individual viral particles. *Proc. Natl. Acad. Sci. USA* 106, 19114-19119.

Jouvenet N, Zhadina M, Bieniasz PD, Simon SM (2011) Dynamics of ESCRT protein recruitment during retroviral assembly. *Nat. Cell Biol.* 13, 394-401.

Ku PI, Miller AK, Ballew J, Sandrin V, Adler FR, Saffarian S (2013) Identification of pauses during formation of HIV-1 virus like particles. *Biophys. J.* 105, 2262-2272.

Ku PI, Bendjennat M, Ballew J, Landesman MB, Saffarian S (2014) ALIX is recruited temporarily into HIV-1 budding sites at the end of Gag assembly. *PLoS one* 9, e96950.

Lee SK, Potempa M, Swanstrom R (2012) The choreography of HIV-1 proteolytic processing and virion assembly. *J. Biol. Chem.* 287, 40867-40874.

Müller B, Daecke J, Fackler OT, Dittmar MT, Zentgraf H, Kräusslich HG (2004) Construction and characterization of a fluorescently labeled infectious human immunodeficiency virus type 1 derivative. *J. Virol.* 78, 10803-10813.

Pettit SC, Henderson GJ, Schiffer CA, Swanstrom R (2002) Replacement of the P1 amino acid of human immunodeficiency virus type 1 Gag processing sites can inhibit or enhance the rate of cleavage by the viral protease. *J. Virol.* 76, 10226-10233.

Prescher J, Baumgärtel V, Ivanchenko S, Torrano AA, Brauchle C, Müller B, Lamb DC (2015) Super-resolution imaging of ESCRT-proteins at HIV-1 assembly sites. *PLoS Pathog.* 11, e1004677.

Rahman SA, Koch P, Weichsel J, Godinez WJ, Schwarz U, Rohr K, Lamb DC, Kräusslich HG, Muller B (2014) Investigating the role of F-actin in human immunodeficiency virus assembly by live-cell microscopy. *J. Virol.* 88, 7904-7914.

Salmon P, Oberholzer J, Occhiodoro T, Morel P, Lou J, Trono D (2000) Reversible immortalization of human primary cells by lentivector-mediated transfer of specific genes. *Mol. Ther.* 2, 404-414.

Schur FK, Hagen WJ, Rumlová M, Ruml T, Müller B, Kräusslich HG, Briggs JA (2015) Structure of the immature HIV-1 capsid in intact virus particles at 8.8 A resolution. *Nature* 517, 505-508.

Sood C, Francis AC, Desai TM, Melikyan GB (2017) An improved labeling strategy enables automated detection of single-virus fusion and assessment of HIV-1 protease activity in single virions. *J. Biol. Chem.* 292, 20196-20207.

Sundquist WI, Kräusslich HG (2012) HIV-1 assembly, budding, and maturation. *Cold Spring Harb. Perspect. Med.* 2, a006924.

Swingler S, Gallay P, Camaur D, Song J, Abo A, Trono D (1997) The Nef protein of human immunodeficiency virus type 1 enhances serine phosphorylation of the viral matrix. *J. Virol.* 71, 4372-4377.

\* cited by examiner

SEQUENCE LISTING

<160> NUMBER OF SEQ ID NOS: 6

<210> SEQ ID NO 1
<211> LENGTH: 396
<212> TYPE: DNA
<213> ORGANISM: Human immunodeficiency virus

<400> SEQUENCE: 1

| | | | | | | |
|---|---|---|---|---|---|---|
| atgggcgccc | gcgcctccgt | gctgtccggc | ggcgagctgg | acagatggga | gaagatccgc | 60 |
| ctgcgccccg | gcggcaagaa | gaagtacaag | ctgaagcaca | tcgtgtgggc | ctcccgcgag | 120 |
| ctggagcgct | tcgccgtgaa | ccccggcctg | ctggagacct | ccgagggctg | ccgccagatc | 180 |
| ctgggccagc | tgcagccctc | cctgcaaacc | ggctccgagg | agctgcgctc | cctgtacaac | 240 |
| accgtcgcca | cgctgtactg | cgtgcaccag | cgcatcgaaa | tcaaggacac | caaggaggcc | 300 |
| ctggacaaga | tcgaggagga | gcagaacaag | tccaagaaga | aggcccagca | ggccgccgcc | 360 |
| gacaccggcc | attccaacca | ggtgtcccag | aactac | | | 396 |

<210> SEQ ID NO 2
<211> LENGTH: 693
<212> TYPE: DNA
<213> ORGANISM: Human immunodeficiency virus

<400> SEQUENCE: 2

| | | | | | | |
|---|---|---|---|---|---|---|
| cccatcgtgc | agaacatcca | gggccagatg | gtgcaccagg | ccatctcccc | ccgcacccctg | 60 |
| aacgcctggg | tgaaggtggt | ggaggagaag | gccttctccc | ccgaagtcat | ccccatgttc | 120 |
| tccgccctgt | ccgagggcgc | cacccccag | acctgaaca | ccatgctgaa | caccgtgggc | 180 |
| ggccaccagg | ccgccatgca | gatgctgaag | gagaccatca | acgaggaggc | cgccgagtgg | 240 |
| gaccgcgtgc | acccgtgca | cgccggcccc | atcgccccg | gccagatgcg | cgagccccgc | 300 |
| ggctccgaca | tcgccggcac | cacctccacc | agtaccctgc | aagagcagat | cggctggatg | 360 |
| acccacaacc | ccccatccc | cgtgggcgag | atctacaagc | gctggatcat | cctgggcctg | 420 |
| aacaagatcg | tgcgcatgta | ctccccccacc | tccatcctgg | acatccgcca | gggccccaag | 480 |
| gagcccttcc | gcgactacgt | ggaccgcttc | tacaagaccc | tgcgcgccga | gcaggcctcc | 540 |
| caggaggtaa | agaactggat | gaccgagacc | ctgctggtgc | agaacgccaa | ccccgactgc | 600 |
| aagaccatcc | tgaaggccct | gggccccggc | gccaccctgg | aggagatgat | gaccgcctgc | 660 |
| cagggcgtgg | gcggcccccgg | ccacaaggcc | cgc | | | 693 |

<210> SEQ ID NO 3
<211> LENGTH: 39
<212> TYPE: DNA
<213> ORGANISM: Human immunodeficiency virus

<400> SEQUENCE: 3

| | | | |
|---|---|---|---|
| gtgctggccg | aggccatgtc | ccaagtcacc | aaccccgcc | 39 |

<210> SEQ ID NO 4
<211> LENGTH: 168
<212> TYPE: DNA
<213> ORGANISM: Human immunodeficiency virus

<400> SEQUENCE: 4

| | | | | | | |
|---|---|---|---|---|---|---|
| accatcatga | tccagaaggg | caacttccgc | aaccagcgca | agaccgtgaa | gtgcttcaac | 60 |
| tgcggcaagg | agggccacat | cgccaagaac | tgccgcgccc | ccgcaagaa | gggctgctgg | 120 |
| aagtgcggca | aggagggcca | ccagatgaaa | gattgtactg | agagacag | | 168 |

```
<210> SEQ ID NO 5
<211> LENGTH: 48
<212> TYPE: DNA
<213> ORGANISM: Human immunodeficiency virus

<400> SEQUENCE: 5
gctaattttt tagggaagat ctggccttcc cacaagggaa ggccaggg              48

<210> SEQ ID NO 6
<211> LENGTH: 165
<212> TYPE: DNA
<213> ORGANISM: Human immunodeficiency virus

<400> SEQUENCE: 6
aattttcttc agagcagacc agagccaaca gccccaccag aagagagctt caggtttggg      60
gaagagacaa caactccctc tcagaagcag gagccgatag acaaggaact gtatcctta     120 gcttccctca gatcactctt tggcagcgac ccctcgtcac aataa                   165
```

METHODS AND COMPOSITIONS FOR A HIV BASED DELIVERY SYSTEM

CROSS-REFERENCE TO RELATED APPLICATIONS

This application claims the benefit of U.S. Provisional Patent Application No. 62/911,812, filed on Oct. 7, 2019, which is incorporated by reference herein in its entirety.

STATEMENT REGARDING FEDERALLY SPONSORED RESEARCH

This invention was made with government support under Grant R01 AI150474 awarded by National Institute of Health. The government has certain rights in the invention.

REFERENCE TO SEQUENCE LISTING

The Sequence Listing submitted Oct. 7, 2020 as a text file named "21101_0367U2_Sequence_Listing.txt," created on Oct. 6, 2020, and having a size of 2,887 bytes is hereby incorporated by reference pursuant to 37 C.F.R. § 1.52(e)(5).

BACKGROUND

HIV virions assemble on the plasma membrane of cells incorporating 2,000 Gag and ~120 Gag-Pol proteins along with HIV accessory proteins and two copies of genomic viral RNA all incorporated within the immature HIV lattice. These immature virions assembly sites recruit Endosomal Sorting Complexes Required for Transport proteins to catalyze their release from the plasma membrane. The released immature virions are however non-infectious. Once released, the viral immature lattice is subject to specific processing by HIV protease to produce the mature infectious virion. Gag and Gag-Pol domains include sequentially matrix (MA), capsid (CA), spacer peptide 1 (SP1), nucleocapsid (NC) domains, which are shared in both Gag and Gag-Pol then respectively, spacer peptide 2 (SP2) and p6 domains in Gag, and transframe (TF), protease (PR), reverse transcriptase (RT) and integrase (IN) domains in Gag-Pol. Efficient release of particles capable of maturation requires timely release of the immature virions before premature activation of the protease which can lead to release of virions void of Pol associated enzymes and therefore non-infectious. During HIV virion assembly, both Gag and Gag-Pol precursors attach to the virion membrane's inner leaflet through the myristylated N-terminus of MA domain. The CA domain harbors most of the interfaces required for formation of both immature as well as mature HIV capsids. The NC domain has primary function in recruiting and packaging genomic RNA and is also reported to interact with cellular factors during assembly. The assembly, release, maturation of HIV requires a complex coordination between many of the viral domain as well as cellular protein interactions. The ability of Gag and Gag-Pol proteins to coordinate a complex release and maturation machinery that leads to delivery of RNA genomes to host cells has been exploited in design of lentiviral vectors which are now routinely used to efficiently deliver exogenous genes into hard to transfect cells in vivo as well as in vitro. Insertion of foreign proteins within this architecture is however, poorly tolerated. The first attempt at creating a fluorescent HIV virion was carried out by inserting a fluorescent protein fused to MA which was later modified to incorporate a cleavage site in between MA and the fluorescent protein, both of these designs only partially support full virion infectivity.

A viral-based vector capable of budding and maturation with similar efficiency to the parental virus and with the ability to serve as a vehicle for nucleic acid, peptide, or protein delivery is needed.

BRIEF SUMMARY

The architecture of the Gag and Gag-Pol domains are evolutionary optimized to support maximum efficiency for release of infectious virions. Disclosed here are composition and methods related to HIV virions capable of budding and maturation with similar efficiency to the parental virus and with the ability to serve as a vehicle for nucleic acid, peptide, or protein delivery.

Described herein are nucleic acid sequences comprising a modified Gag sequence wherein the modified Gag sequence comprises an exogenous sequence of interest between the nucleocapsid domain and the SP2 region which can help encode the proteins suitable to assemble into a lentivirus with an exogenous protein of interest integrated that has similar infectivity to native lentivirus.

Disclosed are nucleic acid sequences comprising a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region.

Disclosed are vectors comprising a nucleic acid sequence, wherein the nucleic acid sequence comprises a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region.

Disclosed are recombinant lentiviruses comprising a nucleic acid sequence comprising a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region.

Disclosed are recombinant cells comprising one or more of the disclosed nucleic acid sequences, virions or recombinant lentiviruses.

Disclosed are methods of producing a recombinant lentivirus comprising transfecting a cell with a plasmid comprising the nucleic acid sequence of one or more of the disclosed nucleic acid sequences in combination with an envelope plasmid.

Disclosed are methods of treating a subject with a therapeutic agent comprising administering to a subject in need thereof a recombinant lentivirus, wherein the recombinant lentivirus comprises one or more of the disclosed nucleic acid sequences, wherein the exogenous sequence of interest encodes a therapeutic agent.

Disclosed are methods of monitoring lentivirus assembly, budding, and/or maturation comprising transfecting a cell with a plasmid comprising any one of the disclosed nucleic acid sequences in combination with an envelope plasmid, wherein the exogenous sequence of interest encodes a detection agent.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figures 1A, 1B, 1C:
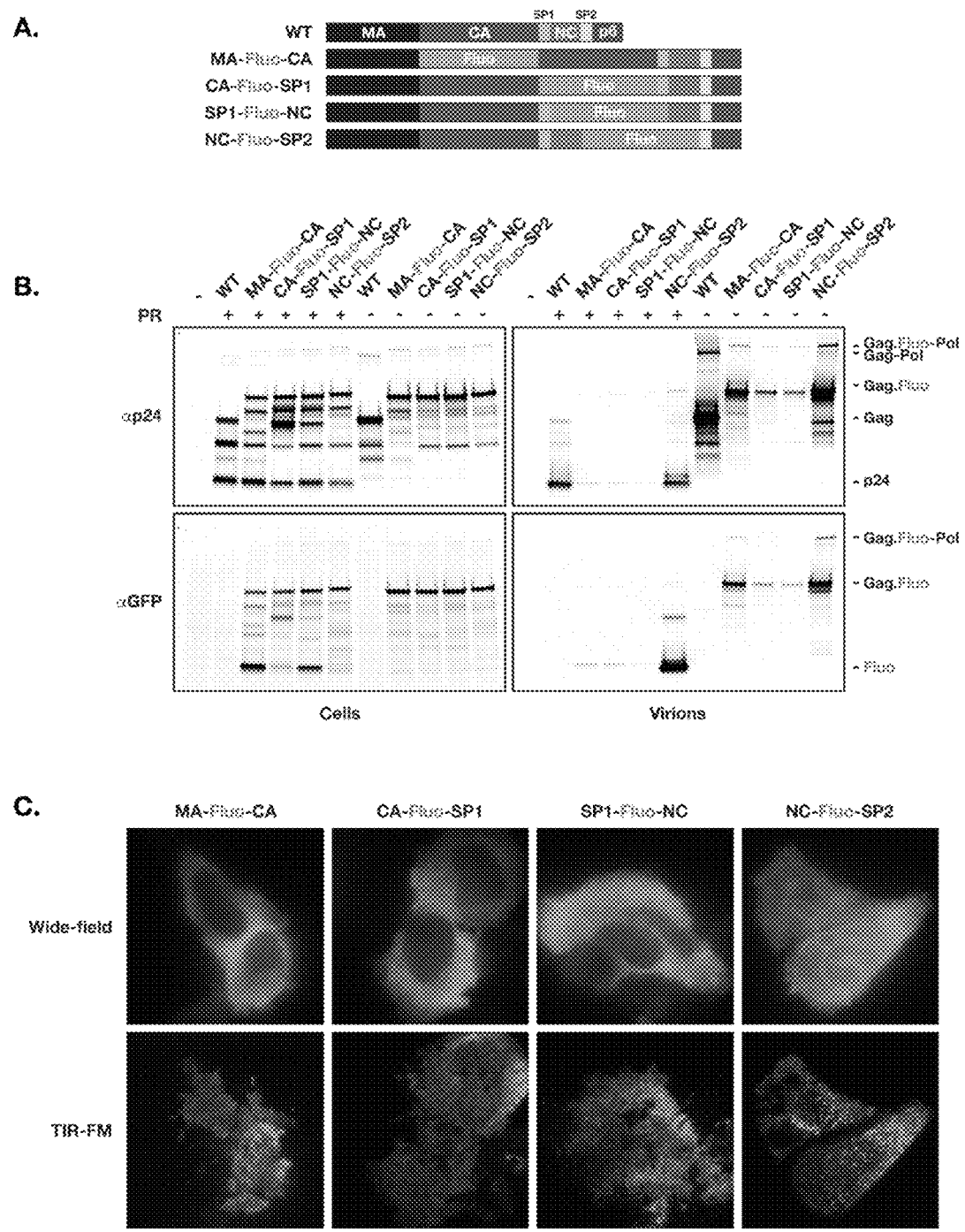
FIGS. 1A, 1B, and 1C show examples of the construction and expression of HIV R8.2:Gag-Fluo vectors. (A) GFP-derived pHluorin (Fluo) is inserted into R8.2 between the domains of Gag as indicated with the protease cleavage sites duplicated accordingly for flanking both ends of the fluorescent protein. (B) Quantitative immunoblot analysis of R8.2 (WT, unlabeled) and R8.2:Gag-Fluo vectors expression using 293T cells. 24 hours post-transfection, cells and virions were collected and analyzed as described in Materials and Methods section. Both R8.2 PR wild type (+; active protease) and PRAD25N (−; inactive protease) were characterized. The specific primary antibodies used for immunoprobing and positions of viral proteins are indicated at left and right, respectively. (C) Cellular expression of R8.2:Gag-Fluo vectors was analyzed using HeLa cells. 12 hours post-transfection, cells were visualized under wide-field imaging to assess cellular expression (cytoplasmic distribution) then under TIR-FM acquisition for evaluating the virions assembly on plasma membranes (dense punctae).

The disclosed methods and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a nucleic acid sequence" includes a plurality of such nucleic acid sequences, reference to "the exogenous sequence" is a reference to one or more exogenous sequences and equivalents thereof known to those skilled in the art, and so forth.

"Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. In some aspects, as referred to herein, a lentivirus that is present outside of a cell is referred to as a virion. Thus "lentivirus" and "virion" can be used interchangeably when referring to the extracellular virus.

As used herein, a "virus" is an infectious agent that consists of protein and nucleic acid, and that uses a host cell's genetic machinery to produce viral products specified by the viral nucleic acid. In some aspects, a virus is found inside of a cell. However, as noted herein, in some aspects, a virus can refer to a virion if present extracellularly.

A "nucleic acid" refers to a polymer of DNA or RNA that is single or double-stranded, linear or circular, and, optionally, contains synthetic, nonnatural, or modified nucleotides, which are capable of being incorporated into DNA or RNA polymers. A DNA polynucleotide preferably is comprised of genomic or cDNA sequences.

A "wild-type strain of a virus" is a strain that does not comprise any human-made mutations, i.e., any virus that can be isolated from nature. Alternatively, a wild-type strain is any virus that has been cultured in a laboratory, but still, in the absence of any other virus, is capable of producing progeny genomes or virions like those isolated from nature. For example, the pNL4-3 HIV molecular clone described in the following Examples is a wild-type strain.

As used herein, vector (or plasmid) refers to elements that are used to introduce nucleic acid sequences into cells for either expression or replication thereof. The vectors typically remain episomal, but can be designed to effect integration of a gene or portion thereof into a chromosome of the genome. Selection and use of such vectors are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, that upon introduction into an appropriate host cell, results in expression of a nucleic acid sequence cloned into the vector. Appropriate expression vectors are well known to those of skill in the art and include those that are replicable in eukaryotic cells and/or prokaryotic cells and those that remain episomal or those which integrate into the host cell genome. In some aspects, the vector is HIV-1 ΔR8.2.

As used herein "virion" refers to an infective form of a virus outside of a host cell in which it was produced. A virion comprises a capsid that surrounds a core of DNA or RNA. In some aspects, the core of DNA or RNA is the viral genome.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Nucleic Acid Sequences

Disclosed are nucleic acid sequences comprising a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region.

In some aspects, the modified HIV Gag sequence comprises wild type sequences for the MA domain, CA domain, SP1 region, NC domain, SP2 region, and p6 domain. In some aspects, a modified HIV Gag sequence is considered modified due to the addition of an exogenous sequence of interest between the NC domain and the SP2 region. Thus, in some aspects, the MA domain, CA domain, SP1 region, NC domain, SP2 region, and p6 domain are sequences from a wild type strain of HIV. In some aspects, a modified HIV Gag sequence can be a modified HIV-1 or HIV-2 Gag sequence. For example, a modified HIV Gag sequence can be from the wild type isolate HIV-$1_{NL4-3}$.

In some aspects, an exogenous sequence of interest is in frame with the modified HIV Gag sequence. Thus, the exogenous sequence of interest can be translated into an exogenous protein of interest at the same time the Gag sequences of MA, CA, NC, and p6 are translated. For example, the exogenous sequence of interest can be translated as part of the Gag polyprotein.

The term "sequence of interest" or "exogenous sequence of interest" can mean a nucleic acid sequence (e.g., a therapeutic gene), that is partly or entirely heterologous, i.e., foreign, to a cell into which it is introduced.

The term "sequence of interest" or "exogenous sequence of interest" can also mean a nucleic acid sequence, that is partly or entirely homologous to an endogenous gene of the cell into which it is introduced, but which is designed to be inserted into the genome of the cell in such a way as to alter the genome (e.g., it is inserted at a location which differs from that of the natural gene or its insertion results in "a knockout"). For example, a sequence of interest can be cDNA, DNA, or mRNA.

The term "sequence of interest" or "exogenous sequence of interest" can also mean a nucleic acid sequence that is partly or entirely complementary to an endogenous gene of the cell into which it is introduced.

A "sequence of interest" or "exogenous sequence of interest" can also include one or more transcriptional regulatory sequences and any other nucleic acid, such as introns, that may be necessary for optimal expression of a selected nucleic acid. A "protein of interest" means a peptide or polypeptide sequence (e.g., a therapeutic protein), that is expressed from a sequence of interest or gene of interest.

In some aspects, an exogenous sequence of interest encodes a therapeutic agent or a detection agent. In some aspects, a therapeutic agent can be a nucleic acid (e.g. cDNA, DNA, RNA, RNAi, or mRNA) or a protein, peptide or polypeptide sequence.

In some aspects, the therapeutic agent can be a cancer therapeutic, an anti-inflammatory, an immune response activator, an immune response inhibitor.

In some aspects, a detection agent can be any agent or moiety that is capable of being detected. As used herein, detect, detected and detecting refer generally to any manner of discovering or determining the presence of a signal, such as visual inspection, microscopy, fluorescence spectroscopy, absorption, reflectance measurement, flow cytometry, magnetic resonance methods such as magnetic resonance imaging (MRI) and magnetic resonance spectroscopy (MRS), ultrasound, X-rays, gamma rays (after annihilation of a positron and an electron in PET scanning), tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography and ultrasonic tomography. Direct detection of a detection agent refers to, for example, measurement of a physical phenomenon, such as energy or particle emission or absorption of the moiety itself, such as by visual inspection, fluorescence microscopy, X-ray, or MRI. Indirect detection refers to measurement of a physical phenomenon, such as energy or particle emission or absorption, of an atom, molecule or composition that binds directly or indirectly to the detection agent. In a non-limiting example of indirect detection, a detection agent can be biotin, which can be detected by binding to avidin. Exemplary detection agents include, but are not limited to, fluorescent moieties, metals such as colloidal gold, iron, gadolinium, and gallium-67, and radionuclides. In some aspects, fluorescent moieties refer to a protein that possesses the ability to fluoresce (i.e., to absorb energy at one wavelength and emit it at another wavelength). Exemplary fluorescent moieties can be, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein. Extending the spectrum of available colors of fluorescent proteins to blue, cyan, orange yellow and red variants, provides a method for multicolor tracking of fusion proteins.

In some aspects, the disclosed nucleic acid sequences can further comprise a flanking sequence between the exogenous sequence of interest and the NC domain and between the sequence of interest and the SP2 region. In some aspects, the disclosed nucleic acid sequences can further comprise a flanking sequence between the 5' end of the exogenous sequence of interest and the 3' end of the NC domain and between the 3' end of the sequence of interest and the 5' end of the SP2 region. In some aspects, the flanking sequence can be a cleavage site. For example, a cleavage site can be a protease cleavage site. Thus, in some aspects, the flanking sequence between the 5' end of the exogenous sequence of interest and the 3' end of the NC domain is a cleavage site. In some aspects, the flanking sequence between the 3' end of the sequence of interest and the 5' end of the SP2 region is a cleavage site.

In some aspects, the disclosed nucleic acid sequences can further comprise HIV pol, tat, and rev genes. In some aspects, the disclosed nucleic acid sequences can further comprise HIV vif and nef genes.

In some aspects, the disclosed nucleic acid sequences can further comprise additional HIV genes that are necessary for virus production with the exception of a functional Env gene.

In some aspects, the disclosed nucleic acid sequences can further comprise a mutated envelope (Env) gene, wherein the mutated Env gene is not capable of being expressed. In some aspects, the disclosed nucleic acid sequences can further comprise an HIV Env gene, and wherein the construct comprises a stop codon before the HIV Env gene. In some aspects, the disclosed nucleic acid sequences do not comprise the HIV Env gene.

In some aspects, the disclosed nucleic acid sequences can comprise the entire HIV genome except the Env gene. In some aspects, the disclosed nucleic acid sequences can comprise the entire HIV genome and wherein the Env gene is mutated.

In some aspects, a modified HIV Gag sequence comprises wild type MA domain, CA domain, SP1 region, NC domain, SP2 region, and/or p6 domains. Examples of wild type MA domain, CA domain, SP1 region, NC domain, SP2 region, and/or p6 domains are:

MA (SEQ ID NO: 1)
ATGGGCGCCCGCGCCTCCGTGCTGTCCGGCGGCGAGCTGGACAGATG

GGAGAAGATCCGCCTGCGCCCCGGCGGCAAGAAGAAGTACAAGCTGA

AGCACATCGTGTGGGCCTCCCGCGAGCTGGAGCGCTTCGCCGTGAAC

CCCGGCCTGCTGGAGACCTCCGAGGGCTGCCGCCAGATCCTGGGCCA

GCTGCAGCCCTCCCTGCAAACCGGCTCCGAGGAGCTGCGCTCCCTGT

ACAACACCGTCGCCACGCTGTACTGCGTGCACCAGCGCATCGAAATC

AAGGACACCAAGGAGGCCCTGGACAAGATCGAGGAGGAGCAGAACAA

GTCCAAGAAGAAGGCCCAGCAGGCCGCCGCCGACACCGGCCATTCCA

ACCAGGTGTCCCAGAACTAC;

CA (SEQ ID NO: 2)
CCCATCGTGCAGAACATCCAGGGCCAGATGGTGCACCAGGCCATCTC

CCCCCGCACCCTGAACGCCTGGGTGAAGGTGGTGGAGGAGAAGGCCT

TCTCCCCCGAAGTCATCCCCATGTTCTCCGCCCTGTCCGAGGGCGCC

ACCCCCCAGGACCTGAACACCATGCTGAACACCGTGGGCGGCCACCA

GGCCGCCATGCAGATGCTGAAGGAGACCATCAACGAGGAGGCCGCCG

AGTGGGACCGCGTGCACCCCGTGCACGCCGGCCCCATCGCCCCCGGC

CAGATGCGCGAGCCCCGCGGCTCCGACATCGCCGGCACCACCTCCAC

CAGTACCCTGCAAGAGCAGATCGGCTGGATGACCCACAACCCCCCCA

TCCCCGTGGGCGAGATCTACAAGCGCTGGATCATCCTGGGCCTGAAC

AAGATCGTGCGCATGTACTCCCCCACCTCCATCCTGGACATCCGCCA

GGGCCCCAAGGAGCCCTTCCGCGACTACGTGGACCGCTTCTACAAGA

CCCTGCGCGCCGAGCAGGCCTCCCAGGAGGTAAAGAACTGGATGACC

GAGACCCTGCTGGTGCAGAACGCCAACCCCGACTGCAAGACCATCCT

GAAGGCCCTGGGCCCCGGCGCCACCCTGGAGGAGATGATGACCGCCT

GCCAGGGCGTGGGCGGCCCCGGCCACAAGGCCCGC;

SP1

(SEQ ID NO: 3)
GTGCTGGCCGAGGCCATGTCCCAAGTCACCAACCCCGCC;

NC (SEQ ID NO: 4)
ACCATCATGATCCAGAAGGGCAACTTCCGCAACCAGCGCAAGACCGT

GAAGTGCTTCAACTGCGGCAAGGAGGGCCACATCGCCAAGAACTGCC

GCGCCCCCGCAAGAAGGGCTGCTGGAAGTGCGGCAAGGAGGGCCAC

CAGATGAAAGATTGTACTGAGAGACAG;

SP2

(SEQ ID NO: 5)
GCTAATTTTTTAGGGAAGATCTGGCCTTCCCACAAGGGAAGGCCAGG

G;

p6

(SEQ ID NO: 6)
AATTTTCTTCAGAGCAGACCAGAGCCAACAGCCCCACCAGAAGAGAG

CTTCAGGTTTGGGGAAGAGACAACAACTCCCTCTCAGAAGCAGGAGC

CGATAGACAAGGAACTGTATCCTTTAGCTTCCCTCAGATCACTCTTT

GGCAGCGACCCCTCGTCACAATAA.

Thus, in some aspects, a modified HIV Gag sequence comprises a MA domain comprising the sequence of SEQ ID NO:1, a CA domain comprising the sequence of SEQ ID NO:2, a SP1 region comprising the sequence of SEQ ID NO:3, a NC domain comprising the sequence of SEQ ID NO:4, a SP2 region comprising the sequence of SEQ ID NO:5, and/or a p6 domain comprising the sequence of SEQ ID NO:6.

In some aspects, a modified HIV Gag sequence can further comprise a modified, or mutated, MA domain, CA domain, SP1 region, NC domain, SP2 region, and/or p6 domain compared to the same sequences from a wild type strain of HIV. In some aspects, a wild type strain of HIV can be HIV-1$_{NL4-3}$. In some aspects, a modified or mutated MA domain, CA domain, SP1 region, NC domain, SP2 region, and/or p6 domain can be a modified or mutant form of SEQ ID NO:1, SEQ ID NO:2, SEQ ID NO:3, SEQ ID NO:4, SEQ ID NO:5, and/or SEQ ID NO:6.

Disclosed are nucleic acid sequences comprising a modified HIV Gag sequence, wherein the modified HIV Gag sequence comprises, from 5' to 3', a MA domain, CA domain, SP1 region, NC domain, SP2 region, and p6 domain, wherein the modified HIV Gag sequence further comprises an exogenous sequence of interest between the NC domain and the SP2 region and wherein the MA domain, CA domain, SP1 region, NC domain, SP2 region, and/or p6 domain of the modified HIV Gag sequence is a variant or derivative of a wild type domain of HIV. In some aspects, any variant or derivative can be used so long as the variant or derivative produces a functional Gag polyprotein. Variants or derivatives that either do not produce a protein or produce a nonfunctional protein are not contemplated herein.

In some aspects, variants or derivatives of HIV pol, tat, and rev genes are present in the compositions disclosed herein. In some aspects, any variant or derivative can be used as long as the variant or derivative produces a functional Pol polyprotein, tat protein or rev protein.

It is understood that one way to define any known variants and derivatives or those that might arise, of the disclosed genes and encoded proteins herein is through defining the variants and derivatives in terms of homology to specific known sequences. Specifically disclosed are variants of the genes and encoded proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to a wild type HIV sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by, for example, the algorithms disclosed in Zuker, M. Science 244:48-52, 1989, Jaeger et al. Proc. Natl. Acad. Sci.

USA 86:7706-7710, 1989, Jaeger et al. Methods Enzymol. 183:281-306, 1989 which are herein incorporated by reference for at least material related to nucleic acid alignment.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Disclosed are nucleic acid constructs encoding a chimeric or recombinant HIV particle that is assembled in a cell, wherein the chimeric HIV particle comprises a modified HIV Gag sequence, wherein the modified HIV Gag sequence comprises from 5' to 3' a matrix domain (MA), capsid (CA) domain, SP1 region, nucleocapsid (NC) domain, SP2 region, and p6 domain, wherein the modified HIV Gag sequence further comprises a sequence of interest between the NC domain and the SP2 region.

C. Vectors

Disclosed are vectors comprising one or more of the disclosed nucleic acid sequences herein. In some aspects, the vector can be HIV ΔR8.2 (R8.2), wherein the disclosed nucleic acids sequences can be incorporated into the HIV ΔR8.2 (R8.2) backbone. R8.2 is derived from full length HIV-1 R9 vector and incorporates all components of R9 except Env and Nef [27].

There are a number of compositions and methods which can be used to deliver nucleic acids to cells, either in vitro or in vivo. These methods and compositions can largely be broken down into two classes: viral based delivery systems and non-viral based delivery systems. For example, the disclosed vectors comprising any of the disclosed nucleic acid sequences can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be any nucleotide construction used to deliver genes or gene fragments into cells (e.g., a plasmid), or as part of a general strategy to deliver genes or gene fragments, e.g., as part of recombinant retrovirus or adenovirus (Ram et al. Cancer Res. 53:83-88, (1993)). For example, disclosed herein are expression vectors comprising a nucleic acid sequence capable of encoding an HIV Gag polyprotein operably linked to a control element.

The “control elements” present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Promoters controlling transcription from vectors in mammalian host cells may be obtained from various sources, for example, the genomes of viruses such as polyoma, Simian Virus 40 (SV40), adenovirus, retroviruses, hepatitis B virus and most preferably cytomegalovirus, or from heterologous mammalian promoters (e.g., beta actin promoter). The early and late promoters of the SV40 virus can be obtained as an SV40 restriction fragment, which also contains the SV40 viral origin of replication (Fiers et al., Nature, 273: 113 (1978)). The immediate early promoter of the human cytomegalovirus can be obtained as a HindIII E restriction fragment (Greenway, P. J. et al., Gene 18: 355-360 (1982)). Additionally, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Examples include, but are not limited to, the SV40 enhancer on the late side of the replication origin (bp 100-270), the cytomegalovirus early promoter enhancer, the polyoma enhancer on the late side of the replication origin, and adenovirus enhancers.

The promoter or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

A promoter or enhancer region can act as a constitutive promoter or enhancer to maximize expression of the polynucleotides of the invention. In certain constructs the promoter or enhancer region can be active in all eukaryotic cell types, even if it is only expressed in a particular type of cell at a particular time. An example of this type of promoter is the CMV promoter (650 bases). Other promoters include, but are not limited to, SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. In some aspects, the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The expression vectors can include a nucleic acid sequence encoding a detection agent (e.g. a marker product). This detection agent can be used to determine if the gene has been delivered to the cell and once delivered is being expressed. Detection agents can include, but are not limited to the *E. coli* lacZ gene, which encodes β-galactosidase, and the gene encoding the green fluorescent protein.

In some embodiments the detection agent may be a selectable marker. Examples of suitable selectable markers for mammalian cells include, but are not limited to, dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR- cells and mouse LTK- cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

As used herein, vectors are agents that transport the disclosed nucleic acid sequences, such as a nucleic acid sequence comprising a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region, into a cell without degradation and include a promoter yielding expression of the gene(s) (e.g. MA, CA, NC, p6) in the cells into which it is delivered. In some aspects, the vectors can be viral or non-viral vectors. Any vector that can be suitable for use in transporting the disclosed nucleic acid sequences can be used.

D. Recombinant Lentivirus

Disclosed are recombinant lentiviruses or virions comprising any of the disclosed nucleic acid sequences. Disclosed herein are recombinant lentiviruses or virions comprising a nucleic acid sequence comprising a modified HIV Gag sequence, wherein the modified HIV Gag sequence comprises, from 5' to 3', a matrix domain (MA), capsid (CA) domain, SP1 region, nucleocapsid (NC) domain, exogenous sequence of interest, SP2 region, and p6 domain. For example, disclosed are recombinant lentiviruses or virions comprising a nucleic acid sequence comprising a modified HIV Gag sequence, wherein the modified HIV Gag sequence comprises, from 5' to 3', a matrix domain (MA), capsid (CA) domain, SP1 region, nucleocapsid (NC) domain, SP2 region, and p6 domain, wherein the modified HIV Gag sequence further comprises an exogenous sequence of interest between the NC domain and the SP2 region.

In some aspects, the virions generated by the disclosed constructs are approximately 165±35 nm in size.

In some aspects, an exogenous sequence of interest encodes a therapeutic agent or a detection agent as disclosed herein. In some aspects, an exogenous sequence of interest encodes an exogenous protein of interest. In some aspects, an exogenous protein of interest is packaged as a part of the Gag and Gag-Pol polyproteins. Thus, in some aspects, during virus maturation, the exogenous protein of interest can be released and is independently present within the lumen of a virion.

Disclosed herein are chimeric Gag proteins comprising an HIV-Gag protein and an exogenous protein of interest, wherein the HIV-Gag protein comprises from the N to C terminus, a matrix domain (MA), capsid (CA) domain, SP1 region, nucleocapsid (NC) domain, exogenous protein of interest, SP2 region, and p6 domain.

Disclosed herein are chimeric HIV particles, wherein the chimeric HIV particle comprises a chimeric HIV Gag protein wherein the HIV-Gag protein comprises from the N to C terminus, a matrix domain (MA), capsid (CA) domain, SP1 region, nucleocapsid (NC) domain, exogenous protein of interest, SP2 region, and p6 domain. In some aspects, the chimeric HIV particle is capable of budding and maturation with similar efficiency to the parental virus (e.g. wild-type HIV).

Also disclosed are pharmaceutical compositions containing any of the compositions disclosed herein. For example, disclosed herein are recombinant lentiviruses and a suitable pharmaceutical carrier. Pharmaceutical compositions provided herein can be in various forms, e.g., in solid, liquid, powder, aqueous, or lyophilized form. Examples of suitable pharmaceutical carriers are known in the art and include but are not limited to water, buffers, saline solutions, phosphate buffered saline solutions, various types of wetting agents, sterile solutions, alcohols, gum arabic, vegetable oils, benzyl alcohols, gelatin, glycerin, carbohydrates such as lactose, sucrose, amylose or starch, magnesium stearate, talc, silicic acid, viscous paraffin, perfume oil, fatty acid monoglycerides and diglycerides, pentaerythritol fatty acid esters, hydroxy methylcellulose, powders, among others. Pharmaceutical compositions provided herein can contain other additives including, for example, antioxidants and preservatives, analgesic agents, binders, disintegrants, coloring, diluents, exipients, extenders, glidants, solubilizers, stabilizers, tonicity agents, vehicles, viscosity agents, flavoring agents, emulsions, such as oil/water emulsions, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as crystalline cellulose, microcrystalline cellulose, citric acid, dextrin, dextrose, liquid glucose, lactic acid, lactose, magnesium chloride, potassium metaphosphate, starch, among others. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

E. Recombinant Cells

Disclosed are recombinant cells comprising one or more of the disclosed nucleic acid sequences, vectors or lentiviruses. In some aspects, the disclosed recombinant cells lines can be cell lines or primary cells. In some aspects, the recombinant cells can be derived from a mammalian cell.

Disclosed are cell lines comprising one or more of the disclosed nucleic acid sequences, vectors or lentiviruses.

F. Methods of Producing Recombinant Lentiviruses

Disclosed are methods of producing one or more of the disclosed recombinant lentiviruses. For example, disclosed are methods of producing a recombinant lentivirus comprising transfecting a cell with a vector comprising the nucleic acid sequence of one or more of the disclosed nucleic acid sequences in combination with an envelope plasmid.

In some aspects, an envelope plasmid is a plasmid or vector that comprises a nucleic acid sequence that encodes an envelope protein. In some aspects, an envelope plasmid comprises a nucleic acid sequence that encodes an envelope protein, wherein the envelope protein is not an HIV envelope protein. In some aspects, an envelope plasmid comprises a nucleic acid sequence that encodes VSV-G. In some aspects, a recombinant lentivirus can be pseudotyped by using any of the known envelopes.

In some aspects, production of recombinant lentiviruses can be achieved using any of the well-known techniques for producing lentivirus. For example, a two plasmids or three plasmids system can be used. In some aspects, a two plasmids system comprises transfecting a cell with a first plasmid comprising a modified HIV Gag sequence, wherein the modified HIV Gag sequence comprises, from 5' to 3', a MA domain, CA domain, SP1 region, NC domain, SP2 region, and p6 domain, wherein the modified HIV Gag sequence further comprises an exogenous sequence of interest between the NC domain and the SP2 region, and comprises all remaining HIV genes necessary for production of HIV except a functional Env gene in combination with a second plasmid comprising a nucleic acid sequence that encodes an envelope protein. In some aspects, all HIV genes necessary for production of HIV includes all HIV genes. In some aspects, all HIV genes necessary for production of HIV includes all HIV genes except non-essential genes such as but not limited to, nef. In some aspects, the Env gene can be present in the first plasmid but mutated to encode a non-functional protein. In some aspects, no Env gene is present in the first plasmid.

Production of recombinant lentiviruses can be achieved using a three plasmids system. In some aspects, a three plasmids system comprises transfecting a cell with a first plasmid comprising a modified HIV Gag sequence, wherein the modified HIV Gag sequence comprises, from 5' to 3', a MA domain, CA domain, SP1 region, NC domain, SP2 region, and p6 domain, wherein the modified HIV Gag sequence further comprises an exogenous sequence of interest between the NC domain and the SP2 region in combination with a second plasmid comprising a nucleic acid sequence that encodes an envelope protein and a third plasmid comprising the remaining HIV genes, besides Gag, and except a functional Env gene. In some aspects, the Env gene can be present in the third plasmid but mutated to encode a non-functional protein. In some aspects, no Env gene is present in the third plasmid.

In some aspects, a three plasmids system comprises transfecting a cell with three plasmids. In some aspects, one plasmid comprises a nucleic acid sequence that encodes an envelope protein. In some aspects, the remaining HIV genes, either with a mutated Env gene or no Env gene, are split between the other two plasmids, wherein one of the remaining two plasmids at least comprises a modified HIV Gag sequence, wherein the modified HIV Gag sequence comprises, from 5' to 3', a MA domain, CA domain, SP1 region, NC domain, SP2 region, and p6 domain, wherein the modified HIV Gag sequence further comprises an exogenous sequence of interest between the NC domain and the SP2 region.

In some aspects, if one of the plasmids comprises an HIV Env gene, the Env gene is a mutated Env gene, wherein the mutated Env gene is not capable of being expressed. For example, in some aspects, if one of the plasmids comprises an HIV env gene, the nucleic acid sequence of the Env gene comprises a stop codon before the end of a wild type HIV Env gene. The presence of the early stop codon can prevent Env from being expressed.

In some aspects, once the recombinant lentivirus has matured away from the cell in which it was produced, it becomes a virion. In some aspects, the virions are purified.

G. Methods of Treating

Disclosed are methods of treating a subject with a therapeutic agent comprising administering to a subject in need thereof one or more of the disclosed recombinant lentiviruses, virions, or recombinant cells.

Disclosed are methods of treating a subject with a therapeutic agent comprising administering to a subject in need thereof a recombinant lentivirus, wherein the recombinant lentivirus comprises one or more of the disclosed nucleic acid sequences, wherein the exogenous sequence of interest encodes a therapeutic agent.

In some aspects, the therapeutic agent can be a DNA, RNA, or protein. In some aspects, the therapeutic agent is an siRNA. In some aspects, the therapeutic agent can be a cancer therapeutic, an anti-inflammatory, an immune response activator, an immune response inhibitor.

In some aspects, upon infection of the recombinant virus in a cell of the subject, the therapeutic agent is released into the cytosol of the cell.

H. Methods of Monitoring

Disclosed are methods of monitoring lentivirus morphogenesis. Virion morphogenesis can be divided into three stages: assembly, budding, and maturation. In some aspects, one or more of these stages can be monitored using one or more of the disclosed nucleic acid sequences.

Disclosed are methods of monitoring lentivirus assembly, budding, and/or maturation comprising transfecting a cell with a plasmid comprising any one of the disclosed nucleic acid sequences in combination with an envelope plasmid, wherein the exogenous sequence of interest encodes a detection agent.

In some aspects, the detection agent can be a fluorescent moiety, metals such as colloidal gold, iron, gadolinium, and gallium-67, and radionuclides. Exemplary fluorescent moieties can be, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein.

In some aspects, the disclosed methods further comprise detecting the detection agent at one or more stages of lentivirus morphogenesis. For example, in some aspects, the detection agent can be detected during virus assembly, budding and/or maturation.

In some aspects, detecting can include any manner of discovering or determining the presence of a signal (directly or indirectly from the detection agent), such as visual inspection, microscopy, fluorescence spectroscopy, absorption, reflectance measurement, flow cytometry, magnetic resonance methods such as magnetic resonance imaging (MRI) and magnetic resonance spectroscopy (MRS), ultrasound, X-rays, gamma rays (after annihilation of a positron and an electron in PET scanning), tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography and ultrasonic tomography.

Because the exogenous sequence of interest (i.e. the detection agent) is expressed as part of the Gag and Gag-Pol polyproteins, it can be used to monitor the assembly stage of morphogenesis. The detection agent will accumulate at the plasma membrane of the cell in which the lentivirus is being produced during the assembly stage since it is part of the Gag polyprotein and the Gag polyprotein assembles at the plasma membrane. In some aspects, budding can be monitored as the detection agent will remain part of the Gag polyprotein during this process. In some aspects, during maturation, the detection agent is cleaved away from the other Gag proteins that make up the Gag polyprotein and the detection agent remains free floating within the lumen of the virion.

I. Kits

The composition and materials described above as well as other materials and compositions can be packaged together in any suitable combination as a kit useful for performing, or aiding in the performance of, the disclosed method. It is useful if the kit components in a given kit are designed and adapted for use together in the disclosed method. For example disclosed are kits for producing a recombinant lentivirus, the kit comprising one or more of the disclosed nucleic acid sequences. The kits also can contain a nucleic acid sequence that encodes an Env protein such as VSV-G.

Examples

A. Materials and Methods

1. Expression Vectors, Cells, and Antibodies.

HIV-1 ΔR8.2 (HIV-1 NL4-3 R9 ΔNEF. ΔENV [27]) was used.

All cell lines used were grown in complete DMEM medium under standard conditions, excepted during TIR-FM experiments where cells were incubated in CO2-independent medium (LifeTechnologies).

Anti-p24 (183-H12-5C, NIH AIDS Reagent Program), anti-GFP (sc-8334, Santa Cruz Biotech.), anti-mCherry (TA150125, Origene), anti-RT (MAb21, NIH AIDS Reagent Program), and infrared dye coupled secondary antibodies (LI-COR) were used for immunoprobing. Scanning was performed with the Odyssey infrared imaging system (LI-COR) in accordance with the manufacturer's instructions at 700 and/or 800 nm, accordingly.

2. Construction of the Fluo-R8.2 Battery.

According to the five major processing sites previously characterized (24), we inserted in frame the fluorescent proteins (Fluo-proteins) in Gag ORF of R8.2 with conserving the sequence of each individual site intact however duplicated for flanking Fluo-proteins at N- and C-terminuses, accordingly.

| Gag sequence: | MA|CA|SP1|NC|SP2|p6    [|: PR cleavage sites] |
|---|---|
| MA-Fluo-CA | MA....SQNY|PIV-Fluo-SQNY|PIV....CA |
| CA-Fluo-SP1 | CA....ARVL|AEA-Fluo-ARVL|AEA....SP1 |
| SP1-Fluo-NC | SP1....ATIM|MQR-Fluo-ATIM|MQR....NC |
| NC-Fluo-SP2 | NC....RQAN|FLGEF-Fluo-RQAN|FLGEF....SP2 |

The Fluo-R8.2-STOP constructs were generated by introducing a translation stop codon immediately after Gag p6 domain.

3. Virion Release Analysis.

293T cells were transfected accordingly using standard CaPO4 precipitation technique. Both cells and media were collected for analysis. Cells were lysed in RIPA buffer (140 mM NaCl, 8 mM Na2HPO4, 2 mM NaH2PO4, 1% NP-40, 0.5% sodium deoxycholate, 0.05% SDS). On the other hand, after removal of residual cell debris by centrifugation, virions were pelleted from cell supernatants by harvesting 2 hours through 10% (w/v) sucrose cushion at 15,000×g, and final virions pellets were re-suspended in PBS. Both cells and virions were analyzed by SDS-PAGE and immunoblotting. Bands intensities were quantified using the LI-COR Image Studio Line software. Virions release yields/ratio were calculated as virions-associated Gag/Gag-Pol forms per cell-associated Gag/Gag-Pol forms based on CA probing.

4. TIR-FM Assessments.

HeLa cells were transfected using Lipofectamine 2000 (LifeTechnologies). Live images were acquired using iMIC Digital Microscope made by TILL photonics controlled by TILL's Live Acquisition imaging software. Laser beam passed through an AOTF (acousto-optical tunable filter) and focused into a fiber that delivers the light to TILL Yanus digital scan head and then Polytrope II optical mode switch. Yanus consists of two galvo-mirrors and one spherical mirror to control the laser beam position. The Polytrope rapidly switches illumination beam path between Epi (wide field), FRAP and TIRF microscopy modes. It also holds the quadrant photodiode used for TIRF penetration depth calibration, which was set to 150 nm for the experiments in this manuscript. In the TIRF mode Yanus is used to control the position of the focused beam in the objective's back focal plane and can be adjusted within 0.2 milliseconds. The focused beam was positioned at the edge of the back focal plane of the objective (N=1.46, 100×, Zeiss) to reach beyond the critical angle and achieve TIRF. TIRF critical angle was verified by scanning the laser beam across the back aperture and measuring the reflection of the laser from the Glass sample interface back into the objective and onto the quadrant photodiode. The penetration depth of the beam is calculated based on the incident angle of the beam that is in turn measured by the position of the beam on the quadrant photodiode. Once the penetration depths for the experiments are set at the beginning of acquisition, a feedback loop keeps the focus of the objective on the sample by constantly monitoring the position of the back-reflected beam with respect to the original beam. The TIRF illumination was also rotated on the objective back focal plane 1 turn/exposure (TIRF360) to maximize homogeneity of the TIRF images.

5. Efficiency of RNA Packaging and Delivery.

Virions were produced using 293T cells grown in 6 cm dishes. Cells were co-transfected following standard CaPO4 precipitation technique with either parental R8.2 (non modified) or R8.2:Gag-Fluo constructs along with pLOX-GFP [28] and pCMV-VSV-G, then media were replaced 4 hours post-transfection with fresh ones. 32 hours later, supernatants were harvested and syringe-filtered through 0.45 μm membranes. Viral titers were estimated using fluorescence-activated cell sorting (FACS) to detect eGFP expression that is driven by the packaged pLOX-GFP mRNAs and transduced in the infected HeLa cells. The infectivity values are relative to the parental R8.2 vector.

6. Infectivity

The supernatant of 293T cells was collected 48 hours after transfection with viral vectors then added to a monolayer of TZM-bl cells. TZM-bl cells were then harvested using britelite plus Reporter Gene Assay (Perkin Elmer). The infectivity was quantified by reading luminescence using the Cytation 5 microscope (ThermoFisher Scientific, Inc.).

7. Electron Microscopy.

HeLa cells were grown on ACLAR disks and transfected with either NL4.3 or NL4.3(NC-Fluo-SP2) vectors. Cells were fixed in 2.5% glutaraldehyde plus 1% paraformaldehyde in 0.1 M Cacodylic buffer for 30 minutes then embedded in Embed 812 kit's resin (Electron Microscopy Sciences), and sectioned at 80 nm with diamond knife (Diatome) using Leica EM UC6 (Leica Microsystems). Sections were visualized using JEM 1400 Plus electron microscope (JEOL, Tokyo, Japan) at 120 kV.

B. Results

1. Insertion of Fluorescent Proteins Between NC and SP2 is Tolerated by HIV for Proper Virion Release and Maturation.

To generate a fully functional fluorescent HIV vector that incorporates fluorescent proteins within the open reading frame of Gag, the HIV ΔR8.2 (R8.2) was used as the backbone. R8.2 is derived from full length HIV-1 R9 vector and incorporates all components of R9 except ENV and NEF [27]. HIV Gag consists of MA, CA, SP1, NC, SP2 and p6 domains. Among other trials, the fluorescent protein open reading frame (ORF) was placed at the junction between Gag specific domains resulting in production of four R8.2: Gag-Fluo vectors: R8.2:Gag (MA-Fluo-CA), R8.2:Gag (CA-Fluo-SP1), R8.2:Gag (SP1-Fluo-NC) and R8.2:Gag (NC-Fluo-SP2) (FIG. 1A).

R8.2:Gag-Fluo vectors were then tested following the virion release assay using 293T cells and harvesting viruses from cell supernatants 24 hours post-transfection. Immunoblots depicted in FIG. 1B show similar protein expression levels from the four R8.2:Gag-Fluo constructs with either active or inactive protease accordingly, however, in comparison to the R8.2 parental virus (WT) only R8.2:Gag(NC-Fluo-SP2) vector produced similar yield of virions released and Gag/Gag-Pol processing as assessed using CA (p24) probing. All other R8.2:Gag-Fluo vectors showed a drastic defective yield of released virions and an alteration of the Gag/Gag-Pol maturation profile as visualized by the CA/Gag precursor ratio in purified virions.

The virions assembly efficiency was further assayed using TIR-FM imaging of transfected HeLa cells 12 hours post-transfection. As shown in FIG. 1C, all three R8.2:Gag-Fluo vectors aside from R8.2:Gag(NC-Fluo-SP2) show low densities of formed virions at the plasma membrane of R8.2:Gag-Fluo expressing cells, which indicated the defect within other three vectors as likely related to nucleation and assembly of virions on the cell surface.

2. Defect in Virion Assembly and Release when Fluorescent Proteins are Inserted Between MA and NC.

Figure 2A:
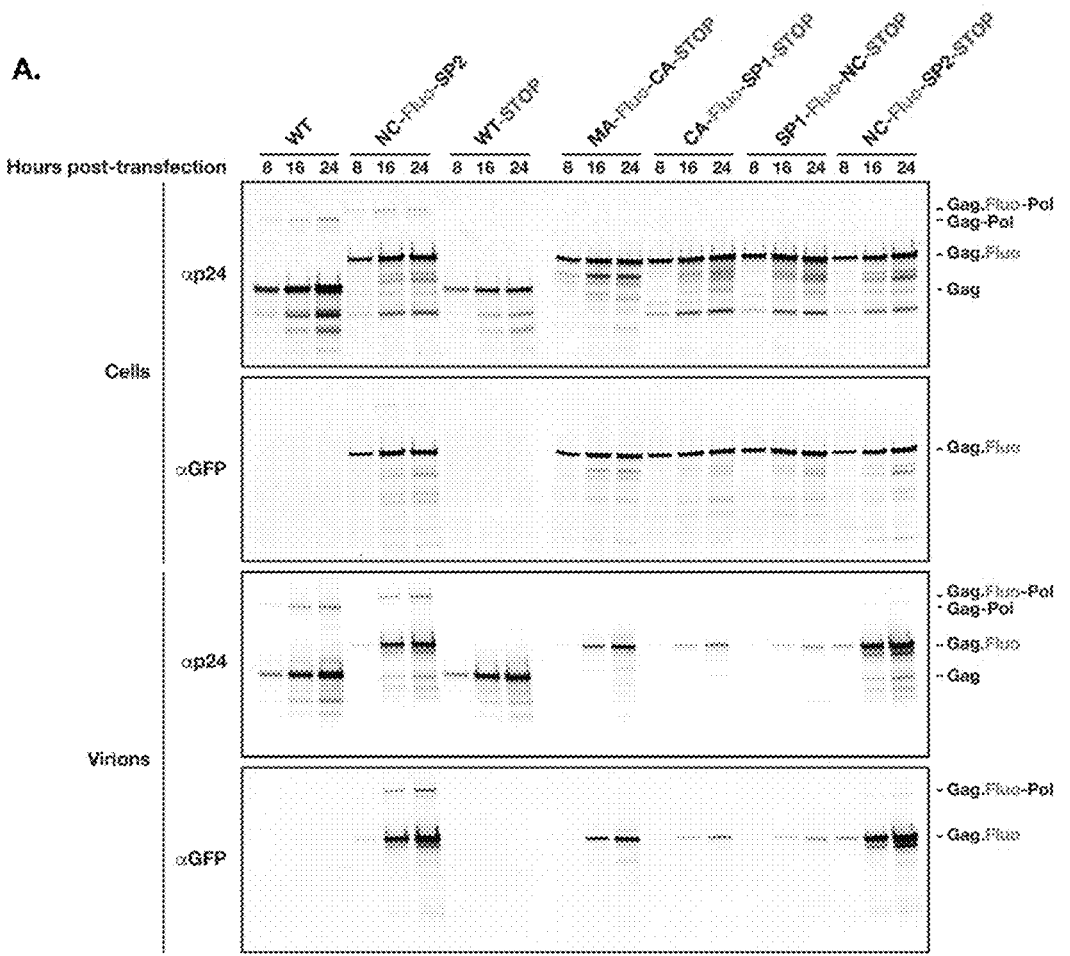
FIGS. 2A and 2B show kinetics of HIV R8.2:Gag-Fluo virions release. (A) The expression in 293T cells of Gag and Gag-Pol proteins are shown by R8.2 PRAD25N and R8.2:Gag(NC-Fluo-SP2) PRAD25N while solely Gag by R8.2-STOP variants in which a stop codon was introduced immediately after Gag p6 domain abrogating therefore Gag-Pol production. Cells and virions were collected and analyzed as described in Materials and Methods section. The specific primary antibodies used for immunoprobing and positions of viral proteins are indicated at left and right, respectively. (B) Densitometry values of the panels shown in (A), which corresponds to the ratio of Gag in virions/cells.
Figure 2B:
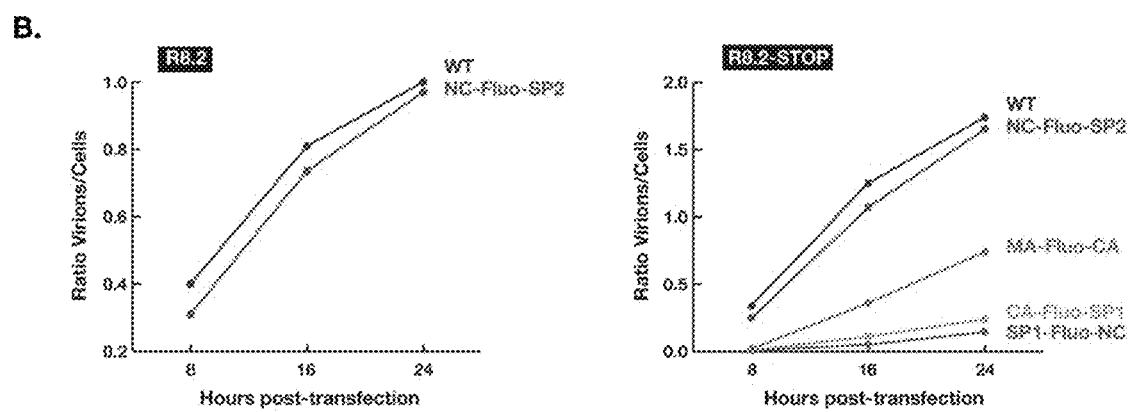

To further test that the insertion of fluo-proteins between Gag MA and NC domains affect negatively the assembly process and therefore the yield of virions produced, a stop codon was inserted in the R8.2:Gag-Fluo vectors immediately after Gag p6 domain (R8.2:Gag-Fluo-STOP) and the kinetics of virion release was analyzed by transfected 293T cells (FIG. 2). R8.2:Gag-Fluo-STOP vectors express only Gag and no Gag-Pol to avoid its potential additional interference during the Gag assembly process. These results clearly shows a dramatic delay in virion release when Fluo-proteins are inserted between CA and NC domains (CA-Fluo-SP1-STOP and SP1-Fluo-NC-STOP) and at a lesser extent, still substantial, when placed between MA and CA domains (MA-Fluo-CA-STOP), while Fluo-proteins insertion between NC and SP2 (NC-Fluo-SP2-STOP) has a minimal effect when compared to the parental unlabeled Gag (WT-STOP). Interestingly, no significant interference of Gag-Pol expression and loading in assembling virions was observed when Fluo-proteins were inserted between NC and SP2 based on the similar time course and yield of virions release (WT versus NC-Fluo-SP2). To this end, for a more accurate comparative analysis between all constructs involved during this specific analysis, the HIV protease was inactivated in the constructs with no stop codon inserted after Gag p6 domain for the stabilization of incorporated Gag-Pol during virions assembly and release.

3. Virions with Insertion of Fluorescent Proteins Between NC and SP2 can Efficiently Carry the GFP Gene to the Host Cell.

Figures 3A, 3B, 3C:
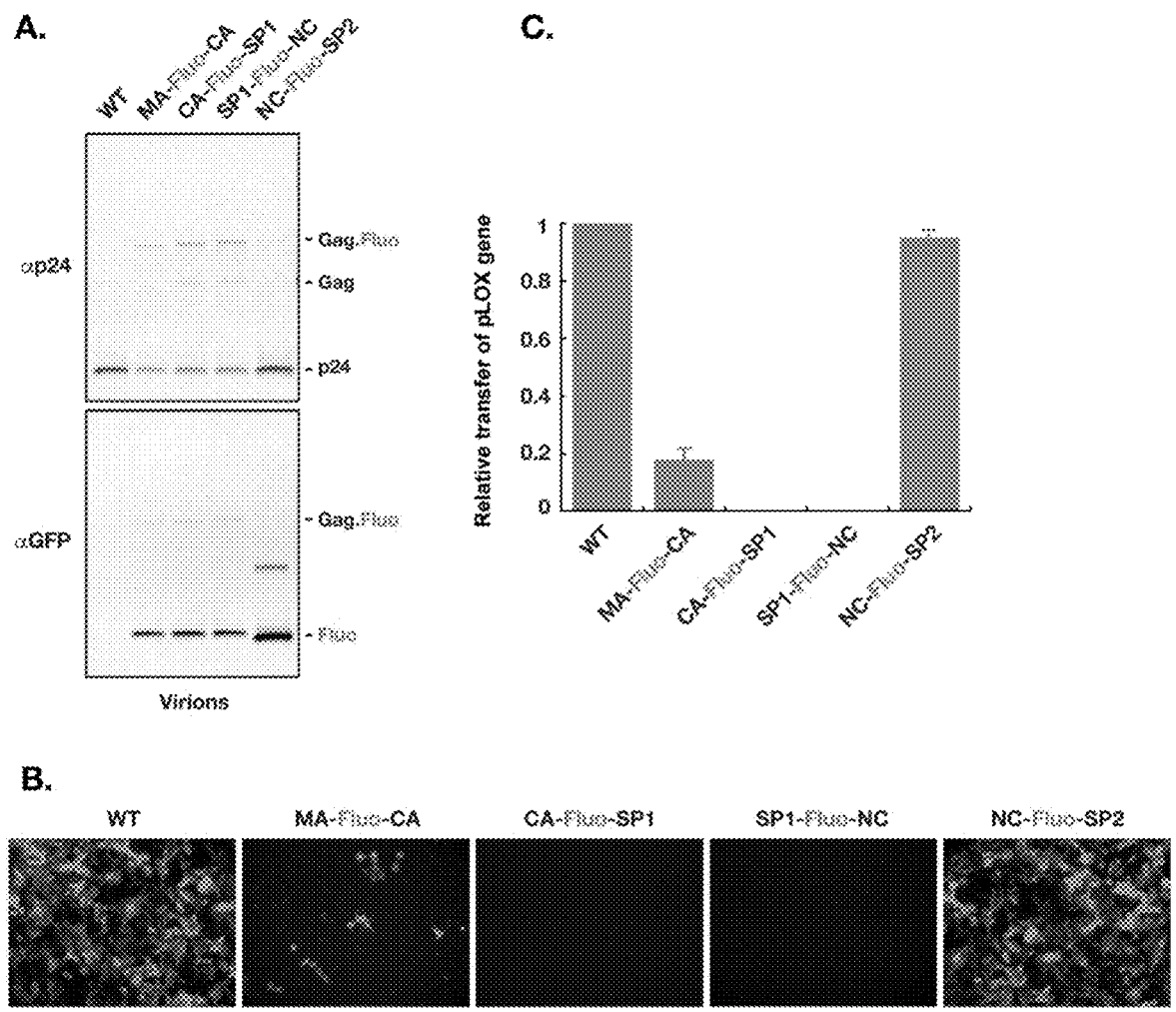
FIGS. 3A, 3B, and 3C show a transfer of pLOX-GFP by R8.2:Gag-Fluo virions. (A) Quantitative calibration of released R8.2:Gag-Fluo virions using immunoblotting. (B) Virions harvested from 293T cells transfected with R8.2 or R8.2:Gag-Fluo vectors along with pLOX-GFP and pCMV-VSV-G plasmids were used to infect a monolayer of HeLa cells. (C) Qualitative assessment of the number of GFP expressing cells in (B).

For rational assessments while analyzing the infectivity potential of each R8.2:Gag-Fluo construct, the virions yield produced by all vectors was first calibrated (FIG. 3A). Interestingly, a clear defect is seen in the virions Gag/Gag-Pol maturation profile of R8.2:Gag(MA-Fluo-CA), R8.2:Gag(CA-Fluo-SP1) and R8.2:Gag(SP1-Fluo-NC) as noticed by the CA(p24)/Gag-Fluo ratios when compared to R8.2 (WT; p24/Gag) and R8.2:Gag(NC-Fluo-SP2; p24/Gag-Fluo). Virions were produced using 293T cells as described in Materials and Methods section, and used either directly (non-calibrated) or after calibration to infect HeLa cells accordingly (FIG. 3B). Fluorescence microscopic evaluation clearly indicate that the parental R8.2 (WT) and R8.2:Gag(NC-Fluo-SP2) are similarly infectious inversely to the rest of R8.2:Gag-Fluo constructs; also, the slight infectivity of R8.2:Gag(MA-Fluo-CA) is reported in the literature (18). Quantification of the infectivity levels of calibrated R8.2:Gag-Fluo virions indicated that R8.2:Gag(NC-Fluo-SP2) vector is ~90% as infectious as the parental R8.2, inversely to the totally inactive R8.2:Gag(CA-Fluo-SP1) and R8.2:Gag(SP1-Fluo-NC) while R8.2:Gag(MA-Fluo-CA) is ~18% (FIG. 3C).

4. Insertion of Fluorescent Protein Between NC and SP2 within NL4.3 does not Support Full Infectivity of Virions.

Figures 4A, 4B, 4C:
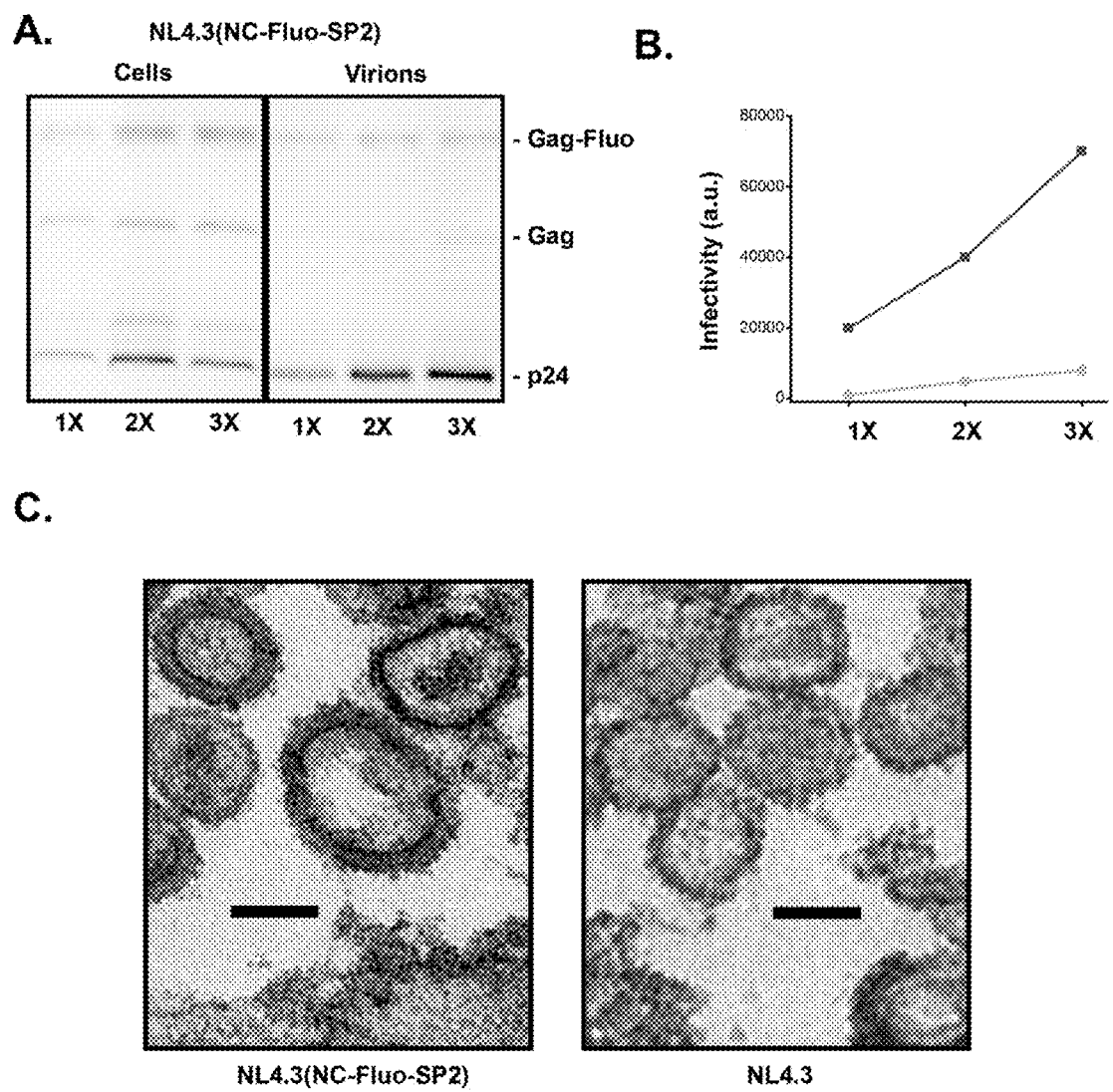
FIGS. 4A, 4B, and 4C show a characterization of NL4.3 (NC-Fluo-SP2) virions. (A) Quantitative calibration of released NL4.3(NC-Flo-SP2) virions using immunoblotting. (B) Virions harvested from 293T cells transfected with NL4.3 (Black) or NL4.3(NC-Flo-SP2) (Gray) vectors were used to infect a monolayer of TZM-bl cells; cells were lysed 24 hours post-infection and infectivity analyzed using luciferase assay. (C) Electron micrograph of virions released from HeLa cells transfected with NL4.3 (Black) or NL4.3 (NC-Flo-SP2). Scale bar represents 100 nm.

To test the ability of the NC-Fluo-SP2 virions in transferring the full HIV genome and supporting full infectivity of the wild type virus, an NL4.3(NC-Fluo-SP2) backbone was generated. As shown in FIG. 4A, the insertion of NC-Fluo-SP2 supports efficient proteolysis of Gag and release of the capsid protein. The released virions however were not as infectious as WT NL4.3 virions as shown in FIG. 4C. Further analysis of the NL4.3(NC-Fluo-SP2) virions revealed highly heterogeneous sizes with an average of 160±35 nm compared to 130±15 nm measured for WT virions. A representative EM image of virions released from HeLa cells plated and transfected on ACLAR is shown in FIG. 4C.

C. Discussion

HIV goes through a sophisticated process of budding and maturation mainly driven by the viral poly-proteins Gag and Gag-Pol. The cellular and viral machineries required for budding and maturation are tightly regulated and synchronized since alterations in their timings result in release of non-infectious HIV virions [9]. These two poly-protein precursors are expressed in the host cell and assemble on the plasma membrane to drive the budding of HIV. After virion release, Gag and Gag-Pol are cleaved to produce MA, CA, NC, PR, RT and IN functional proteins within the lumen of the virus. This design allows the ratio metric incorporation of CA and NC, components of the mature viral capsid, as well as incorporation of PR, RT and IN, which are essential HIV enzymes that defines the infectivity of HIV. Decades of evolution has ensured the proper function of all HIV proteins through their precise incorporation in the Gag and Gag-Pol precursors, therefore previous attempts in creating space for a fluorescent protein to be inserted in their vicinity have stayed only partially successful [25, 26].

Previous trials in making a fluorescent HIV focused on insertion of the fluorescent proteins in between MA and CA domains with the fluorescent protein either permanently fused to MA domain [25] or flanked with the natural HIV PR processing site that bridge MA and CA domains [26]. In the first case, the HIV construct is partially infectious and has a significant defect in maturation however the infectivity is restored when co-expressed along the parental virus [25]. In the second case a SQNY|PIV protease site is duplicated to fit in between MA and the fluorescent protein so that it could be released from the confines of Gag during maturation. To this end, this construct is substantially less infectious than the wild type vector in agreement with a recent report [30]; in addition it has a defect in the yield of virion release and Gag/Gag-Pol precursor maturation (FIGS. 1 and 3).

Insertion of the fluorescent protein anywhere in between MA and NC domains negatively affect the assembly process of Gag and Gag-Pol during the virions budding, which is likely linked to an inefficient Gag polymerization during the virions assembly (FIGS. 1 and 2). The finding that the viral proteins can tolerate the insertion of a foreign protein in between NC and SP2 domains of Gag indicates that all Gag-Gag interactions including MA, CA and NC need to be preserved for the optimal assembly, budding and infectivity.

The finding that the disclosed construct preserves the fluorescent protein after release from Gag post-PR cleavage in the produced progeny virions shed light on a very exciting opportunity to use this vector as an efficient protein delivery tool. Indeed, an average of 2,000 (from Gag-recombinant) plus ~120 (from Gag-recombinant-Pol) recombinant protein of interest would be carried by the virion for delivery.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Briggs, J. A. G.; Kräusslich, H. G., The Molecular Architecture of HIV. *Journal of Molecular Biology* 2011, 410, (4), 491-500.
2. Strack, B.; Calistri, A.; Craig, S.; Popova, E.; Gottlinger, H. G., AIP1/ALIX Is a Binding Partner for HIV-1 p6 and EIAV p9 Functioning in Virus Budding. *cell* 2003, 114, (6), 689-699.
3. VerPlank, L.; Bouamr, F.; LaGrassa, T. J.; Agresta, B.; Kikonyogo, A.; Leis, J.; Carter, C. A., Tsg101, a homologue of ubiquitin-conjugating (E2) enzymes, binds the L domain in HIV type 1 Pr55 Gag. *Proceedings of the National Academy of Sciences* 2001, 98, (14), 7724-7729.
4. Garrus, J. E.; von Schwedler, U. K.; Pornillos, O. W.; Morham, S. G.; Zavitz, K. H.; Wang, H. E.; Wettstein, D. A.; Stray, K. M.; Cote, M.; Rich, R. L.; Myszka, D. G.; Sundquist, W. I., Tsg101 and the Vacuolar Protein Sorting Pathway Are Essential for HIV-1 Budding. *cell* 2001, 107, (1), 55-65.

5. Martin-Serrano, J.; Zang, T.; Bieniasz, P. D., HIV-1 and Ebola virus encode small peptide motifs that recruit Tsg101 to sites of particle assembly to facilitate egress. *Nat Med* 2001, 7, (12), 1313-1319.
6. Martin-Serrano, J.; Yaravoy, A.; Perez-Caballero, D.; Bieniasz, P. D., Divergent retroviral late-budding domains recruit vacuolar protein sorting factors by using alternative adaptor proteins. *Proceedings of the National Academy of Sciences* 2003, 100, (21), 12414-12419.
7. Gottlinger, H. G.; Sodroski, J. G.; Haseltine, W. A., Role of capsid precursor processing and myristoylation in morphogenesis and infectivity of human immunodeficiency virus type 1. *Proceedings of the National Academy of Sciences* 1989, 86, (15), 5781-5785.
8. Lee, S. K.; Potempa, M.; Swanstrom, R., The Choreography of HIV-1 Proteolytic Processing and Virion Assembly. *Journal of Biological Chemistry* 2012, 287, (49), 40867-40874.
9. Bendjennat, M.; Saffarian, S., The Race against Protease Activation Defines the Role of ESCRTs in HIV Budding. *PLoS Pathogens* 2016, 12, (6), e1005657.
10. Saad, J. S.; Miller, J.; Tai, J.; Kim, A.; Ghanam, R. H.; Summers, M. F., Structural basis for targeting HIV-1 Gag proteins to the plasma membrane for virus assembly. *Proceedings of the National Academy of Sciences* 2006, 103, (30), 11364-11369.
11. Vlach, J.; Eastep, G. N.; Ghanam, R. H.; Watanabe, S. M.; Carter, C. A.; Saad, J. S., Structural basis for targeting avian sarcoma virus Gag polyprotein to the plasma membrane for virus assembly. *Journal of Biological Chemistry* 2018, 293, (49), 18828-18840.
12. Hill, C. P.; Worthylake, D.; Bancroft, D. P.; Christensen, A. M.; Sundquist, W. I., Crystal structures of the trimeric human immunodeficiency virus type 1 matrix protein: implications for membrane association and assembly. *Proceedings of the National Academy of Sciences* 1996, 93, (7), 3099-3104.
13. Ganser, B. K.; Li, S.; Klishko, V. Y.; Finch, J. T.; Sundquist, W. I., Assembly and Analysis of Conical Models for the HIV-1 Core. *Science* 1999, 283, (5398), 80-83.
14. Ganser-Pornillos, B. K.; Yeager, M.; Sundquist, W. I., The structural biology of HIV assembly. *Current Opinion in Structural Biology* 2008, 18, (2), 203-217.
15. Pornillos, O.; Ganser-Pornillos, B. K.; Yeager, M., Atomic-level modelling of the HIV capsid. *Nature* 2011, 469, (7330), 424-427.
16. Wagner, J. M.; Zadrozny, K. K.; Chrustowicz, J.; Purdy, M. D.; Yeager, M.; Ganser-Pornillos, B. K.; Pornillos, O., Crystal structure of an HIV assembly and maturation switch. *eLife* 2016, 5, e17063.
17. von Schwedler, U. K.; Stray, K. M.; Garrus, J. E.; Sundquist, W. I., Functional Surfaces of the Human Immunodeficiency Virus Type 1 Capsid Protein. *Journal of Virology* 2003, 77, (9), 5439-5450.
18. Briggs, J. A. G.; Johnson, M. C.; Simon, M. N.; Fuller, S. D.; Vogt, V. M., Cryo-electron Microscopy Reveals Conserved and Divergent Features of Gag Packing in Immature Particles of Rous Sarcoma Virus and Human Immunodeficiency Virus. *Journal of Molecular Biology* 2006, 355, (1), 157-168.
19. Mattei, S.; Tan, A.; Glass, B.; Müller, B.; Kräusslich, H. G.; Briggs, J. A. G., High-resolution structures of HIV-1 Gag cleavage mutants determine structural switch for virus maturation. *Proceedings of the National Academy of Sciences* 2018, 115, (40), E9401-E9410.
20. Berkowitz, R. D.; Goff, S. P., Analysis of Binding Elements in the Human Immunodeficiency Virus Type 1 Genomic RNA and Nucleocapsid Protein. *Virology* 1994, 202, (1), 233-246.
21. D'Souza, V.; Summers, M. F., How retroviruses select their genomes. *Nature Reviews Microbiology* 2005, 3, (8), 643-655.
22. Keane, S. C.; Heng, X.; Lu, K.; Kharytonchyk, S.; Ramakrishnan, V.; Carter, G.; Barton, S.; Hosic, A.; Florwick, A.; Santos, J.; Bolden, N. C.; McCowin, S.; Case, D. A.; Johnson, B. A.; Salemi, M.; Telesnitsky, A.; Summers, M. F., Structure of the HIV-1 RNA packaging signal. *Science* 2015, 348, (6237), 917-921.
23. Dussupt, V.; Javid, M. P.; Abou-Jaoudé, G.; Jadwin, J. A.; de La Cruz, J.; Nagashima, K.; Bouamr, F., The Nucleocapsid Region of HIV-1 Gag Cooperates with the PTAP and LYPX$_n$L Late Domains to Recruit the Cellular Machinery Necessary for Viral Budding. *PLoS Pathog* 2009, 5, (3), e1000339.
24. Naldini, L.; Blömer, U.; Gallay, P.; Ory, D.; Mulligan, R.; Gage, F. H.; Verma, I. M.; Trono, D., In Vivo Gene Delivery and Stable Transduction of Nondividing Cells by a Lentiviral Vector. *Science* 1996, 272, (5259), 263-267.
25. Müller, B.; Daecke, J.; Fackler, O. T.; Dittmar, M. T.; Zentgraf, H.; Krausslich, H. G., Construction and Characterization of a Fluorescently Labeled Infectious Human Immunodeficiency Virus Type 1 Derivative. *Journal of Virology* 2004, 78, (19), 10803-10813.
26. Hübner, W.; Chen, P.; Portillo, A. D.; Liu, Y.; Gordon, R. E.; Chen, B. K., Sequence of Human Immunodeficiency Virus Type 1 (HIV-1) Gag Localization and Oligomerization Monitored with Live Confocal Imaging of a Replication-Competent, Fluorescently Tagged HIV-1. *Journal of Virology* 2007, 81, (22), 12596-12607.
27. Swingler, S.; Gallay, P.; Camaur, D.; Song, J.; Abo, A.; Trono, D., The Nef protein of human immunodeficiency virus type 1 enhances serine phosphorylation of the viral matrix. *Journal of Virology* 1997, 71, (6), 4372-7.
28. Salmon, P.; Oberholzer, J.; Occhiodoro, T.; Morel, P.; Lou, J.; Trono, D., Reversible Immortalization of Human Primary Cells by Lentivector-Mediated Transfer of Specific Genes. *Mol Ther* 2000, 2, (4), 404-414.
29. D. L. D, C.; Klug, A., Physical Principles in the Construction of Regular Viruses. *Cold Spring Harbor Symposia on Quantitative Biology* 1962, 27.
30. Sood, C.; Francis, A. C.; Desai, T. M.; Melikyan, G. B., An improved labeling strategy enables automated detection of single-virus fusion and assessment of HIV-1 protease activity in single virions. *Journal of Biological Chemistry* 2017, 292, (49), 20196-20207.
31. Carlson, L. A.; de Marco, A.; Oberwinkler, H.; Habermann, A.; Briggs, J. A. G.; Kräusslich, H. G.; Grünewald, K., Cryo Electron Tomography of Native HIV-1 Budding Sites. *PLoS Pathog* 2010, 6, (11), e1001173.
32. Sundquist, W. I.; Krausslich, H. G., HIV-1 Assembly, Budding, and Maturation. *Cold Spring Harbor Perspectives in Medicine* 2012, 2, (8).
33. Briggs, J. A. G.; Riches, J. D.; Glass, B.; Bartonova, V.; Zanetti, G.; Kräusslich, H. G., Structure and assembly of immature HIV. *Proceedings of the National Academy of Sciences* 2009, 106, (27), 11090-11095.

We claim:

1. A nucleic acid construct comprising a nucleic acid sequence encoding a modified HIV Gag polypeptide, wherein the modified HIV Gag polypeptide comprises from the N terminus to C-terminus a matrix domain (MA), capsid (CA) domain, SP1 region, nucleocapsid (NC) domain, exogenous peptide, SP2 region, and p6 domain.

2. The nucleic acid construct of claim 1, wherein the nucleic acid sequence encoding the exogenous peptide is in frame with the nucleic acid sequence encoding the modified HIV Gag polypeptide.

3. The nucleic acid construct of claim 1, wherein the exogenous peptide is a therapeutic agent.

4. The nucleic acid construct of claim 1, wherein the nucleic acid sequence encoding the modified HIV Gag polypeptide further comprises a flanking sequence between the nucleic acid sequence encoding the exogenous peptide and the NC domain and a flanking sequence between the nucleic acid sequence encoding the exogenous peptide and the SP2 region.

5. The nucleic acid construct of claim 1, wherein the nucleic acid construct further comprises HIV Pol, Tat, and Rev genes.

6. The nucleic acid construct of claim 1, wherein the nucleic acid construct further comprises HIV Vif and Nef genes.

7. The nucleic acid construct of claim 1, wherein the nucleic acid construct further comprises a mutated Env gene, wherein the mutated Env gene is not capable of being expressed.

8. The nucleic acid construct of claim 1, wherein the nucleic acid construct further comprises an HIV Env gene, and wherein the construct comprises a stop codon before the HIV Env gene.

9. The nucleic acid construct of claim 1, wherein the nucleic acid construct does not comprise the HIV Env gene.

10. The nucleic acid construct of claim 1, wherein the nucleic acid construct is a vector.

11. A method of producing a recombinant lentivirus comprising transfecting a cell with a plasmid comprising the nucleic acid construct of claim 1 in combination with an envelope plasmid.

12. The method of claim 11, wherein:
   (i) the nucleic acid construct further comprises HIV Pol, Tat, and Rev genes; or
   (ii) the nucleic acid construct further comprises HIV Vif and Nef genes; and wherein the nucleic acid construct comprises a mutate Env gene that is not capable of being expressed.

13. The method of claim 11, wherein the nucleic acid construct further comprises an Env gene and:
   (i) HIV Pol, Tat, and Rev genes; or
   (ii) HIV Vif and Nef genes;
   and wherein the nucleic acid comprises a stop codon before the HIV Env gene.

14. The method of claim 11, wherein the envelope plasmid comprises a nucleic acid sequence that encodes VSV-G.

15. A recombinant cell comprising the nucleic acid construct of claim 1.

16. The recombinant cell of claim 15, wherein the recombinant cell is a mammalian cell.

17. A recombinant lentiviral vector comprising a nucleic acid sequence encoding a modified HIV Gag polypeptide, wherein the modified HIV Gag polypeptide comprises from the N terminus to C terminus a matrix domain (MA), capsid (CA) domain, SP1 region, nucleocapsid (NC) domain, exogenous peptide, SP2 region, and p6 domain.

18. A method of expressing a peptide in a subject comprising administering to a subject a lentiviral vector, wherein the lentiviral vector comprises the nucleic acid construct of claim 1.

19. A method of monitoring lentivirus assembly, budding, or maturation comprising transfecting a cell with a plasmid comprising the nucleic acid construct of claim 1 in combination with an envelope plasmid, wherein the exogenous peptide is a detection agent.

20. The method of claim 19, wherein the detection agent is a fluorescent protein.

21. The method of claim 19, further comprising detecting the detection agent at one or more stages of lentivirus morphogenesis.

* * * * *